United States Patent
Kim et al.

(10) Patent No.: US 9,023,607 B2
(45) Date of Patent: May 5, 2015

(54) METHOD FOR EARLY DIAGNOSIS OF ALZHEIMER'S DISEASE USING PHOTOTRANSISTOR

(75) Inventors: Kwan-Su Kim, Seoul (KR); Cheol-Joo Chae, Daejeon (KR); Jae-Min Kang, Seoul (KR); Jeong-Dae Suh, Daejeon (KR); Myung-Ae Chung, Daejeon (KR); Ki-Bong Song, Daejeon (KR)

(73) Assignee: Intellectual Discovery Co., Ltd., Seoul (KR)

( * ) Notice: Subject to any disclaimer, the term of this patent is extended or adjusted under 35 U.S.C. 154(b) by 112 days.

(21) Appl. No.: 13/093,152

(22) Filed: Apr. 25, 2011

(65) Prior Publication Data
US 2011/0262934 A1    Oct. 27, 2011

(30) Foreign Application Priority Data

Apr. 26, 2010  (KR) .................. 10-2010-0038611
Dec. 16, 2010  (KR) .................. 10-2010-0129333

(51) Int. Cl.
*C12Q 1/00*    (2006.01)
*B82Y 15/00*   (2011.01)
*G01N 33/68*   (2006.01)

(52) U.S. Cl.
CPC ............ *B82Y 15/00* (2013.01); *G01N 33/6896* (2013.01); *G01N 2800/2821* (2013.01)

(58) Field of Classification Search
USPC ............. 422/68.1, 82.01, 82.05; 435/7.1, 7.2, 435/7.21, 7.5, 287.1, 287.2, 288.7; 436/501, 518, 526, 537, 807, 809, 171; 977/773, 904, 920, 927
See application file for complete search history.

(56) References Cited

U.S. PATENT DOCUMENTS

| | | | |
|---|---|---|---|
| 5,719,033 A * | 2/1998 | Ackley et al. | 435/7.92 |
| 6,743,581 B1 * | 6/2004 | Vo-Dinh | 506/39 |
| 7,332,353 B2 * | 2/2008 | Baudry et al. | 436/526 |
| 7,763,250 B2 * | 7/2010 | Rosenthal et al. | 424/152.1 |
| 2009/0123459 A1 | 5/2009 | Jung et al. | |
| 2011/0020459 A1 * | 1/2011 | Achrol et al. | 424/520 |
| 2011/0024642 A1 * | 2/2011 | Tredwell et al. | 250/370.09 |
| 2011/0184696 A1 * | 7/2011 | Tung et al. | 702/172 |

FOREIGN PATENT DOCUMENTS

| | | | |
|---|---|---|---|
| KR | 10-2009-0039864 A | | 4/2009 |
| KR | 10-2009-0110101 A | | 10/2009 |
| WO | WO 2008029374 A2 * | | 3/2008 |

\* cited by examiner

*Primary Examiner* — Melanie Y Brown
*Assistant Examiner* — Erik B Crawford
(74) *Attorney, Agent, or Firm* — Rabin & Berdo, P.C.

(57) ABSTRACT

A method for diagnosing Alzheimer's disease by detecting the presence of beta-amyloid in cells using a phototransistor device. Cells that potentially contain beta-amyloid are provided and labeled with a multi-protein that selectively binds to beta-amyloid if present and that includes streptavidin, biotin and polyethylene glycol connected in sequence with the streptavidin being bound to a magnetic bead and the polyethylene glycol being bound to the beta-amyloid, to provide labeled cells. A phototransistor device including a channel layer is provided and a difference in photocurrent determined corresponding to incident light measured before and after selectively fixing the labeled cells on a surface of the channel layer by applying an external magnetic field effective to attract the magnetic bead to the phototransistor device through a permanent magnet positioned below the channel. Any difference between the first and second photocurrents indicates the presence of, and optionally amount of, labeled beta-amyloid in the cells.

6 Claims, 3 Drawing Sheets

METHOD FOR EARLY DIAGNOSIS OF ALZHEIMER'S DISEASE USING PHOTOTRANSISTOR

BACKGROUND OF THE INVENTION

1. Field of the Invention

The present invention relates to a method for diagnosing Alzheimer's disease and, particularly, to a method for diagnosing Alzheimer's disease at an early stage.

2. Description of the Related Art

Dementia is a brain injury that has a seriously malignant influence on personal activity. Among the most common forms of senile dementia is Alzheimer's disease, which is a neurodegenerative disease involving problems with the executive functions of thinking, memory and language.

Much is known about the cause of Alzheimer's, but not comprehensively. No therapeutics that can cure the disease have been discovered thus far. Administration with drugs such as tacrine (Cognex), donepezil (Aricept), rivastigmin (Exelon), or galanthamine (Razadyne, also conventionally known as Reminyl) only temporarily mitigates the progression of Alzheimer's disease in patients in the early or moderate stages.

Alzheimer's disease is characterized by cognitive impairment and is caused by the deposition of beta-amyloid plaques and the formation of neurofibrillary tangles (NFTs) inside nerve cell bodies of brain cell.

Many therapies exist and are developed trying to treat Alzheimer's disease through various approaches. In contrast, relatively fewer studies have been done with regard to simple methods for the early diagnosis of Alzheimer's disease.

For example, Korean Patent Application Publication No. 2009-0048192 discloses a method for the diagnosis of Alzheimer's disease in which the expression level of Fcγ-receptor IIb is measured.

Conceived from the finding that Fcγ-receptor IIb is directly involved in the signal transduction of beta-amyloid, this invention pertains to the diagnosis, prevention and treatment of Alzheimer's disease and a screening method of Alzheimer's disease, characterized by determining the expression level of Fcγ receptor IIb.

In the patent publication, the expression level of Fcγ-receptor IIb can be determined by using a fluorescence detection method in which a fluorescent or color compound is conjugated to a compound binding specifically to Fcγ-receptor IIb and is quantitatively measured.

Also in this patent publication, when an antibody specific to Fcγ-receptor IIb is used, the antibody is allowed to react with a secondary antibody conjugated to a fluorescent substance, is washed, and is analyzed by using a fluorescence microscope or scanner. When a compound specific to Fcγ-receptor IIb is used, the bound compound may be quantified in a bound or separated state.

Korean Patent No. 10-0903526 describes a biosensor using a field effect transistor for detecting a specific biomolecule.

As disclosed in this patent, the FET-type biosensor that can detect the presence of or determine the concentration of a specific biomolecule on the basis of the principle of a field effect transistor (FET) is fabricated by forming a self-assembled monolayer on a passivation layer deposited over a metal thin layer, thus taking advantage of all conditions available for CMOS integrated circuit processes.

Korean Patent Application Publication No. 10-2009-0110101 discloses a method for patterning nerve cells using magnetic nanoparticles, in which an external magnetic field is applied to magnetic nanoparticle-containing nerve cells to induce the extension of neurites.

This method has an advantage over conventional methods, in that it needs not use specific chemicals and cell scaffolds and can be applied to various kinds of cells irrespective of cell types or tissue properties.

In recent years, the early diagnosis of Alzheimer's disease has been implemented by determining the expression level of beta-amyloid, presumed to be the greatest cause of Alzheimer's disease, under a microscope or by analyzing its gene, in association with a fluorescent material.

Being based on optical or chemical techniques, however, conventional diagnosis methods of Alzheimer's disease suffer from the disadvantage of being difficult to perform in real time and requiring high costs for diagnosis. Further, related diagnosis kits of Alzheimer's disease are difficult to produce on a mass scale.

SUMMARY OF THE INVENTION

Accordingly, the present invention has been made keeping in mind the above problems occurring in the prior art, and an object of the present invention is to provide a method for the early diagnosis of Alzheimer's disease using a phototransistor.

In the method of the present invention, cells in which a protein biomarker characteristic of Alzheimer's disease, preferably beta-amyloid, is labeled with magnetic beads, are selectively located in the channel region of a phototransistor, and a difference in photocurrent between normal cells and the cells comprising the protein biomarker labeled with magnetic beads is sensed to diagnose Alzheimer's disease in an early stage.

The above object could be accomplished by the provision of a method for the early diagnosis of Alzheimer's disease, using a phototransistor and a cell with a magnetic bead-labeled biomarker introduced thereinto.

In greater detail, the method for the early diagnosis of Alzheimer's disease using a phototransistor comprises:

setting in place the phototransistor being capable of sensing differences in the level of the photocurrents according to the intensity of incident light, said phototransistor comprising a channel layer;

selectively fixing cells on the surface of the channel layer;

sensing a difference of the photocurrents induced by the cells fixed on the channel layer to diagnose Alzheimer's disease, wherein each of the cells contains a protein biomarker that is causative of Alzheimer's disease and the protein biomarker is labeled with a magnetic bead associated with a multi-protein, wherein the labeling is through selective binding of said multi-protein to the protein biomarker.

As described above, a phototransistor is used to sense cells containing a biomarker that is characteristic of or causative of Alzheimer's disease, preferably beta-amyloid, and a magnetic bead, thus performing the early diagnosis of Alzheimer's disease.

The method according to the present invention allows Alzheimer's disease in an early stage to be readily diagnosed compared to conventional techniques using fluorescent dyes or gene analysis, and enables the quantitative analysis of cells or beta-amyloid by using a change in the intensity of the photocurrents of the phototransistor.

Because it takes advantage of a silicon-processing technique, the phototransistor useful in the present invention can be easily applied to other electronic devices, thus making a great contribution to the development of inexpensive diagnosis kits for Alzheimer's disease.

Also, the present invention finds various applications in the understanding and monitoring of Alzheimer's disease and in pharmaceutical experiments for drug efficiency.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
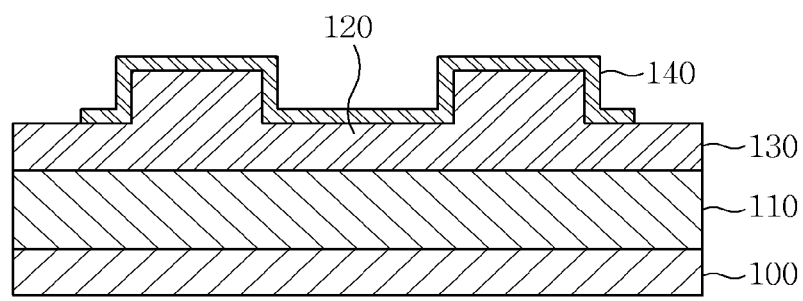
FIG. 1 is of schematic diagrams showing the structure of a phototransistor and profiles of photocurrents generated by the phototransistor.
Figure 1:
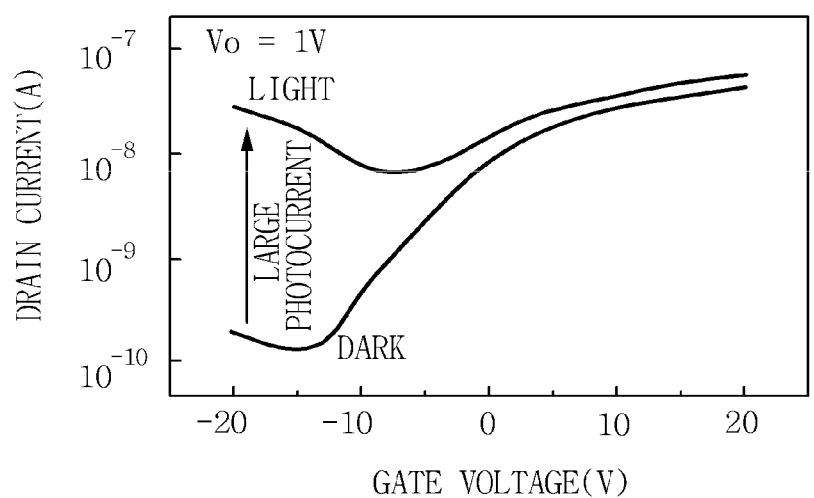

The present invention pertains to a method for the early diagnosis of Alzheimer's disease using a phototransistor, comprising:

setting in place the phototransistor capable of sensing difference in the level of the photocurrents according to the intensity of incident light, said phototransistor comprising a channel layer;

selectively fixing cells on the surface of the channel layer;

sensing a difference of the photocurrents induced by the cells fixed on the channel layer to diagnose Alzheimer's disease, wherein each of the cells contain a protein biomarker that is causative of Alzheimer's disease and the protein biomarker is labeled with a magnetic bead associated with a multi-protein, wherein the labeling is through selective binding of said multi-protein to the protein biomarker.

For use as the protein biomarker characteristic of Alzheimer's disease, beta-amyloid is preferable.

So long as it accumulates beta-amyloid proteins therein, any cell may be used in the present invention. Although no particular limitations are imparted thereto, the cells useful in the present invention are preferably selected from the group consisting of brain cells, olfactory cells, gustatory cells, and visual cells.

The multi-protein is composed of streptavidin, biotin and polyethylene glycol which are connected in sequence, with the streptavidin bound to a magnetic bead.

In addition, the method for the early diagnosis of Alzheimer's disease using a phototransistor in accordance with the present invention is characterized by the use of, as a signal detection label, the magnetic bead bound to the multi-protein in which the polyethylene glycol moiety is associated with beta-amyloid.

As used herein, the term "magnetic bead" means a ferromagnetic bead. Although no particular limitations are imparted thereto, the magnetic bead is preferably selected from among $Fe_2O_3$, $Fe_3O_4$, FePt, CoPt, etc., with a diameter of from 50 nm to 5 μm.

In the method for the early diagnosis of Alzheimer's disease using a phototransistor in accordance with the present invention, an external magnetic field is applied to the phototransistor to locate cells containing the magnetic beads selectively at channel regions of the phototransistor.

In order to generate a magnetic field for the selective location of magnetic bead-containing cells at the channel region, a permanent magnet may be positioned below the channel region.

The channel region of the phototransistor may be composed of a thin film of either amorphous silicon or polycrystalline silicon.

Protecting the phototransistor, an insulation layer made of $SiO_2$, $Si_3N_4$, PMMA, etc. is deposited over the channel layer.

One or more phototransistors may be used in the present invention or the phototransistor may have an array structure.

The method for the early diagnosis of Alzheimer's disease using a phototransistor in accordance with the present invention is characterized in that a change in the photocurrent generated depending on the cells located at the channel region is used as a signal detection label.

In the present invention, a cell in which a protein biomarker that is causative or characteristic of Alzheimer's disease, preferably, beta-amyloid is labeled with a magnetic bead is selectively positioned on the channel layer of the phototransistor, followed by sensing a difference in photocurrent intensity due to the cell.

Hereinafter, the preferred embodiments of the present invention will be described in detail while referring to the accompanying drawings. Throughout the drawings, the same reference numerals are used to refer to the same or similar elements. Moreover, descriptions of known techniques, even if they are pertinent to the present invention, are regarded as unnecessary and may be omitted when they would make the characteristics of the invention and the description unclear. Furthermore, the embodiments of the present invention will be provided for a more perfect description of the present invention for the benefit of those with ordinary knowledge in the art. Therefore, elements in the drawings may be exaggerated in morphology and size to give a more precise description.

FIG. 1 shows the structure of a phototransistor device useful in the early diagnosis of Alzheimer's disease in accordance with the present invention and its photocurrent profile. As seen in FIG. 1, the phototransistor has a simple structure comprising an amorphous silicon channel layer on an insulation film of, e.g., $SiO_2$, or $Si_3N_4$, source and drain electrodes, and a passivation layer for protecting the surface thereof.

When light is incident thereon, the phototransistor having the amorphous silicon channel layer generates a large photocurrent. The generated light varies in intensity depending on the presence of the cells containing beta-amyloid and magnetic beads on the amorphous silicon channel layer. Thus, difference in the intensity of photocurrent can be used for the early diagnosis of Alzheimer's disease.

Figure 2:
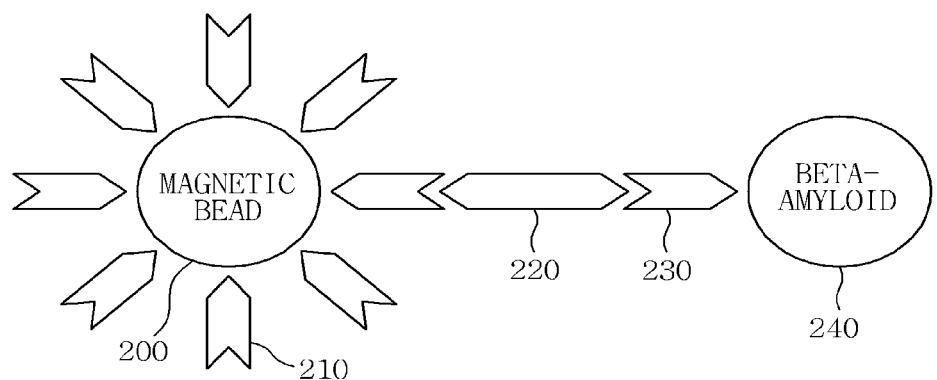
FIG. 2 is a schematic diagram showing the coupling of magnetic beads with beta-amyloid.

The use of a phototransistor in detecting beta-amyloid that is causative of Alzheimer's disease requires the selective association of beta-amyloid with a magnetic bead. In this context, streptavidin molecules bound to a magnetic bead bonded selectively with biotin molecules which are associated via a linker such as poly(ethylene glycol) with beta-amyloid, as shown in FIG. 2.

Figure 3:
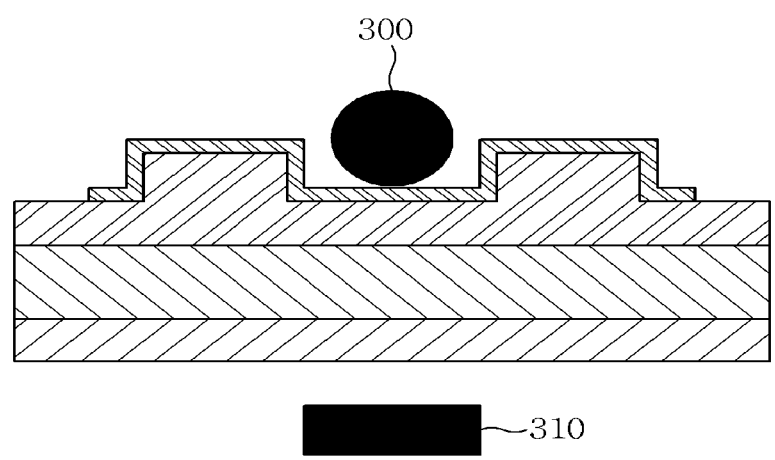
FIG. 3 is a schematic view showing cell patterning using a permanent magnet.

In the phototransistor, the location of cells at the amorphous silicon channel regions is requisite for examining whether the cells contain the beta-amyloid and magnetic beads. Typically, chemical or physical surface treatment is performed for patterning cells. In the present invention, however, a permanent magnet is positioned below the amorphous silicon channel, as shown in FIG. 3, to generate a magnetic field which allows the cells containing beta-amyloid and magnetic beads therein to be fixed at the channel regions.

Accordingly, cells containing beta-amyloid and magnetic beads therein are positioned specifically at the amorphous silicon channels, and photocurrents are generated at different intensities depending on the presence of the cells.

Figure 4:
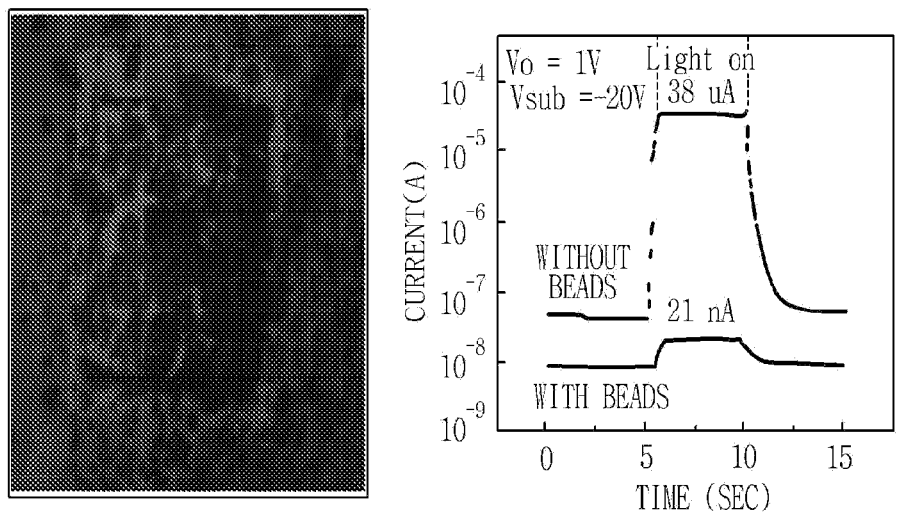
FIG. 4 is of views showing a diagnosis method using a phototransistor.

FIG. 4 shows signal detection by a phototransistor using amorphous silicon as a channel. Magnetic beads with a diameter of 2.8 μm are selectively positioned at channel regions using an external permanent magnet. Characteristic photocurrent profiles are shown according to the presence and absence of the magnetic beads. The absence of the magnetic beads at the channel regions allows large photocurrents to be generated.

In contrast, when the magnetic beads are selectively located on the channels, they block the light incident on the channels, thus showing a low photocurrent profile. Therefore, after cells containing magnetic beads and beta-amyloid are located selectively at channel regions, photocurrents may be measured to diagnose Alzheimer's disease in an early stage.

In addition, the reduction in photocurrent intensity by the cells located on the channel may be analyzed to determine the number of the cells or the amount of beta-amyloid.

DESCRIPTION OF NUMERICAL SYMBOLS

100: Si Substrate
110: SiO$_2$ layer
120: Amorphous-Si layer
130: Metal electrode
140: Passivation layer
200: Magnetic bead
210: Streptavidin
220: Biotin
230: Poly(ethylene glycol)
240: Beta-amyloid
300: Cell containing beta-amyloid and magnetic bead therein
310: Magnetic material Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for diagnosing Alzheimer's disease by detecting the presence of beta-amyloid in cells using a phototransistor device, comprising:
    providing cells that potentially contain beta-amyloid;
    labeling the cells with a multi-protein that selectively binds to beta-amyloid if present and that includes streptavidin, biotin and polyethylene glycol connected in sequence with the streptavidin being bound to a magnetic bead and the polyethylene glycol being directly bound to the beta-amyloid if present, to provide labeled cells;
    providing a phototransistor device for sensing a photocurrent level according to intensity of incident light, said phototransistor device including a channel layer;
    illuminating the phototransistor and sensing a first photocurrent corresponding to the incident light;
    selectively fixing said labeled cells on a surface of the channel layer by applying an external magnetic field effective to attract the magnetic bead to the phototransistor device through a permanent magnet positioned below the channel layer;
    illuminating the phototransistor and sensing a second photocurrent corresponding to said incident light after the labeled cells, if any, are fixed on the surface of the channel layer; and
    detecting any difference between the first and second photocurrents so that the presence of, and optionally amount of, labeled beta-amyloid in said cells is indicated and Alzheimer's disease may be diagnosed.

2. The method as set forth in claim 1, wherein a the magnetic bead has a diameter ranging between 50 nm and 5 μm.

3. The method as set forth in claim 1, wherein the phototransistor device is composed of one or more phototransistors optionally arranged as an array.

4. The method as set forth in claim 1, wherein the cells provided are selected from the group consisting of brain cells, olfactory cells, gustatory cells, visual cells and a combination thereof.

5. The method as set forth in claim 1, wherein the channel layer comprises either amorphous silicon or polycrystalline silicon.

6. The method as set forth in claim 5, wherein the phototransistor further comprises an insulation layer comprising SiO$_2$, Si$_3$N$_4$, or PMMA deposited over the channel layer; source and drain electrodes; and a passivation layer.

* * * * *